USOO5614502A

United States Patent [19]
Flotte et al.

[11] Patent Number: 5,614,502
[45] Date of Patent: Mar. 25, 1997

[54] HIGH-PRESSURE IMPULSE TRANSIENT DRUG DELIVERY FOR THE TREATMENT OF PROLIFERATIVE DISEASES

[75] Inventors: Thomas J. Flotte, Boston; Apostolos Doukas, Belmont; Daniel J. McAuliffe, Boxford; Therese M. Anderson, Brookline, all of Mass.

[73] Assignee: The General Hospital Corporation, Boston, Mass.

[21] Appl. No.: 236,265

[22] Filed: May 2, 1994

Related U.S. Application Data

[63] Continuation of Ser. No. 6,064, Jan. 15, 1993, abandoned.
[51] Int. Cl.$^6$ .............................. A61K 31/70; C07C 6/00; A61N 1/00; A61N 7/00
[52] U.S. Cl. ................. 514/34; 204/157.15; 204/157.62; 424/9.61; 514/410; 540/145; 607/2; 607/3; 607/61; 607/72
[58] Field of Search .................... 204/157.62, 157.15; 514/410, 34; 540/145; 424/9.61; 607/2, 3, 61, 72

[56] References Cited

U.S. PATENT DOCUMENTS

| | | | |
|---|---|---|---|
| 4,649,151 | 3/1987 | Dougherty et al. | 514/410 |
| 4,656,186 | 4/1987 | Bommer et al. | 514/410 |
| 4,658,023 | 4/1987 | Shudo | 540/145 |
| 4,675,338 | 6/1987 | Bommer et al. | 514/410 |
| 4,971,991 | 11/1990 | Umemura et al. | 514/410 |
| 4,994,014 | 2/1991 | Gordon | 600/13 |
| 5,380,411 | 2/1995 | Schlief | 204/157.15 |

OTHER PUBLICATIONS

Holmes et al., "Altered Neutrophil Permeability Following Shock Wave Exposure In Vitro", J. Urology, 147:733–737, 1992.

Berens et al., Effect of Acoustic Shock Waves on Clonogenic Growth and Drug Sensitivity of Human Tumor Cells In Vitro, J. Urology 142:1090–1094, 1989.

Holmes et al., The Combined Effects of Shock Waves and Cisplatin Therapy on Rat Prostate Tumors, J. Urology 144:159–163, 1990.

Randazzo et al., The in Vitro and in Vivo Effects of Extracorporeal Shock Waves on Malignant Cells, Urol. Res. 16:419–426,1988.

Russo et al., High Energy Shock Waves Suppress Tumor Growth In Vitro and In Vivo, J. Urol. 135:626–628, 1986.

Umemura et al., Mechanism of Cell Damage by Ultrasound in Combination with Hematoporphyrin, Jpn. J. Cancer Res. 81:962–966, 1990.

Vivino et al., Stable Cavitation at Low Ultrasonic Intensities Induces Cell Death and Inhibits $^3$H–TdR Incorporation by Con–A–Stimulated Murine Lymphocytes In Vitro, Ultrasound Med. Biol. II:751–759, 1985.

Yumita et al., Synergistic Effect of Ultrasound and Hematoporphyrin on Sarcoma 180, Jpn. J. Cancer Res. 81:304–308, 1990.

McCormack et al. Eur. J. Surg. Oncol., 19(3),pp. 232–234, (1993).

Oosterhof et al. Ultrasound Med Biol., 17(4), pp. 302–399, (1991).

Yumita et al. Jpn. J. Cancer Res., vol. 80, 219–222, (1989).

Primary Examiner—John Kight
Assistant Examiner—Howard C. Lee
Attorney, Agent, or Firm—Fish & Richardson P.C.

[57] ABSTRACT

A method of treating diseases of cell proliferation in a patient such as neoplasms and rheumatoid arthritis including administering sub-toxic doses of a compound in combination with high pressure impulse transients. Methods are also provided for identifying compounds and impulse transient dosages useful for high pressure impulse transient chemotherapy.

13 Claims, 3 Drawing Sheets

HIGH-PRESSURE IMPULSE TRANSIENT DRUG DELIVERY FOR THE TREATMENT OF PROLIFERATIVE DISEASES

STATEMENT AS TO FEDERALLY SPONSORED RESEARCH

This invention was made with Government support under Contract N00014-91-C-0084 awarded by the Department of the Navy. The Government has certain rights in the invention.

Partial funding for the work described herein was provided by the U.S. Government, which has certain rights to the invention.

This is a continuation of application Ser. No. 08/006,064, filed Jan. 15, 1993, now abandoned.

BACKGROUND OF THE INVENTION

The invention relates to the use of compounds in combination with high pressure impulse transients for the treatment of diseases of cell proliferation including both neoplasms and inflammatory diseases.

Photodynamic therapy is the use of light in combination with chemotherapy for the treatment of diseases of cell proliferation. The use of a cytotoxic drug causes cell death to the target tissue when exposed to light (Henderson and Dougherty, *Photochem-Photobiol.* 55:145–57, 1992; Wieman and Fingar, *Surg. Clin. North. Am.* 72:609–22, 1992). The target localization of the chemotherapeutic compound provides the first level of selectivity. The drug need not be localized with absolute specificity to the target tissue because of the activation by light; rather, it need only localize relative to the surrounding tissue. The drug must be non-toxic in the dark but should become toxic in the presence of light. The toxicity is generally, but not always, mediated by oxygen radicals. The drugs can have single functional units as in rhodamine dyes (Shea et al., *Cancer Res.* 49:3961–5, 1989), or the drugs can have separate units as in antibody-chromophore conjugates (Oseroff et al., *Proc. Natl. Acad. Sci. U.S.A.* 83:8744–8, 1986). The second level of localization comes from the distribution of activating light. The area of the body to be treated is illuminated to activate the drug in the specific region. The drug is not activated in the non-illuminated areas of the body even if it has accumulated in these locations and, thus, does not cause significant morbidity. Major current limitations of this technology include the limited light penetration of the tissue, the light dosimetry, and the choice of wavelengths of light is limited by the absorption of the chromophore.

The interaction of laser radiation with tissue can lead to generation of pressure waves (e.g., Cleary, Laser Applications in *Biology and Medicine* 3:175–219, 1977). Depending upon the type of interaction, pressure waves can be either acoustic waves, i.e., low pressure waves propagating with the speed of sound, or shock waves, i.e., high pressure waves propagating at supersonic speed (e.g., Hutchins, *Physical Acoustics* 18:21–123, 1988). The latter are generated when the absorption of laser radiation is followed by a rapid phase change of the medium such as evaporation or formation of plasma. The salient feature of a shock wave is a fast rise which for all practical purposes amounts to a discontinuity in pressure, density, particle velocity (the displacement velocity behind the shock front) and internal energy (e.g., Duval and Fowles, High Pressure *Physics and Chemistry* 2:201–291, 1963). In water, the rise time of a shock wave, up to 100 kbar, is of the order of a picosecond which corresponds to a shock front thickness of 2–5 nm (Harris and Presles, *J. Chem. Phys.* 77:5157–5164, 1982).

The effects of laser-induced pressure waves on tissue have been the subject of extensive research, especially at these effects pertain to laser applications in ophthalmology (e.g., Richardson et al., *Ophthalmol.* 92:1387–1395, 1985; Zysset et al., *Lasers Surg. Med.* 9:193–204, 1989; Vogel et al., *IEEE J. Quant. Electr. QE* 26:2240–2260, 1990).

Ara et al. (*Lasers Surg. Med.* 10:52–59 (1990)) have studied the effects of irradiation of cells that have incorporated melanin particles. Although these experiments have established the importance of laser-induced pressure waves as a cause of cellular injury, the characteristics and the magnitude of the generated pressure waves in situ were not known, so that no quantitative conclusions could be drawn.

Tissue and cell damage, induced by pressure waves from extracorporeal lithotriptors, have been extensively studied (e.g. Russo et al. 1987; Delius et al., *Ultrasound Med. Biol.* 14:117–122, 1988; Brauner et al., *Ultrasound Med. Biol.* 15:451–460, 1989; Cartensen et al., *Ultrasound Med. Biol.* 16:687–698, 1990; Gambihler et al., *Ultrasound Med. Biol.* 16:587–594, 1990; Brummer et al., *J. Stone Dis.* 4:243–248, 1992)). Brummer et al., (*Ultrasound Med. Biol.* 15:229–239, (1989)) have conducted a thorough study of the L1210 mouse leukemia cells in suspension subjected to pressure waves of up to 386 bar. Approximately 70% of the cells in the cultures subjected to this pressure were damaged after 1000 pulses. Cells immobilized in gels, under otherwise identical conditions, showed no histological damage and only minor decrease in viability. These experiments demonstrated that cavitation during irradiation was responsible for the cell damage. In a recent study Prat et al. (*Cancer Research* 51:3024–3029, (1991)) have administered gas microbubbles in order to increase the toxicity of the shock waves, showing that cavitation was the primary mechanism of cell injury.

Russo et al. (*J. Urol.* 135:626–628, (1986); *J. Urol.* 137:338–341, (1987)) exposed tumor nodules to pressure waves in vivo. The nodules did not show any histological changes. The treatment, however, caused retardation in the growth of the tumor. In addition, Carstensen and coworkers (Carstensen et al, *Ultrasound Med. Biol.* 16:687–698, 1990; Hartman et al., *Ultrasound Med. Biol.* 16:581–585, 1990) have demonstrated the effects of pressure waves on Drosophila larvae and chick embryos. They have shown that the number of deaths and malfunctions increased when chick embryos were subjected even to moderate pressure. Furthermore, in the latter experiments a membrane was used to separate the pressure wave from the cavitation. These experiments suggest that the observed biological effects may be induced by effects other than cavitation, e.g., pressure waves.

Several investigators have utilized the combination of pressure impulses and drugs. Holmes et al. (*J. Urol.* 144:159–163, 1990) describe the use of between 2000 and 4000 high pressure, short-duration pulse waves in combination with cisplatinum for the treatment of prostate tumors in rats. Although delayed tumor growth was achieved, an increase in animal mortality from 9% with cisplatinum alone to 29% with cisplatinum combined with shockwave therapy was observed. Berens et al. (*J. Urol.* 142:1090–1094, 1989) describe the use of spark-induced pressure impulses followed by therapy with several chemotherapeutic agents decrease tumor cell proliferation. Randazzo et al. (*Urol. Res.* 14:419–426, 1988) used several drugs followed significantly later by shock waves. This regimen produced enhancement with doxorubicin but not cisplatinumo Vivino et al. (*Ultrasound Med. Biol.* II:751–759, 1985) describe the use ultrasound and Russo et al. (*J. Urol.* 135:626–628, 1986) describe the use of a large number of shock waves alone to kill cells. Umemura et al. (*Jpn. J. Cancer Res.* 81:962–966, 1990) and Yumita et al. (*Jpn. J. Cancer Res.* 81:304–308, 1990) demonstrate the use of continuous wave ultrasound and hematoporphyrin to enhance tumor death.

SUMMARY OF THE INVENTION

The invention features a method of treating a patient with a disease characterized by proliferation of diseased tissue. This method involves administering to the patient a therapeutic compound in combination with high-pressure impulse transients. The administration of the impulse transients is localized to the region of the diseased tissue and the impulses are administered when the level of the compound in the surrounding healthy tissues is less than 50 percent of the level of the compound present in the diseased tissue.

Preferably, the compound administered is a salicylate compound, an antibiotic compound, a light actuated dye compound, or a cytotoxic compound such as cisplatinum or adriamycin. The impulse transients may be administered extracorporeally or during invasive surgery.

The diseases which may usefully be treated using the methods of the invention include diseases involving both neoplasms and inflammatory processes. Neoplasms which may be treated include but are not limited to solid tumors, particularly ovarian carcinomas, brain tumors and breast carcinomas; leukemias/lymphomas; sarcomas; and metastatic carcinomas. Inflammatory processes which may be treated include but are not limited to collagen vascular diseases, particularly including rheumatoid arthritis and lupus erythematosus; vasculitis; diseases associated with vascular proliferation including psoriasis and ophthalmic neovascularization; and chronic infections such as osteomyelitis.

Compounds are administered to a patient using guidelines for administration which will produce greater concentrations of the drugs in the target tissues relative to the surrounding tissue, while maintaining adequate levels of the drug in the target. In general, this differential drug localization can be achieved using guidelines for administration determined using standard techniques known in the field of pharmacology for determining a drug clearance time course. The ratio of drug in the affected tissue to drug in the surrounding tissue must be 2:1 or greater.

Systemically administered compounds which are useful in the invention are those which are taken up in greater amounts and/or retained substantially longer in the proliferating tissues relative to the surrounding tissues of a patient. Compounds with this characteristic can be defined as those which have a useful therapeutic index for high pressure impulse induced cell killing of at least 50. In addition, useful compounds preferably have a therapeutic ratio for high pressure impulse induced killing of at least 10. The therapeutic index is defined by the ratio of the toxicity of compound and high pressure impulses: toxicity of compound alone. The therapeutic ratio is defined as the toxicity of the compound and the impulse in diseased proliferating tissue: toxicity of the compound and the impulse in normal tissue. Toxicity is defined as cell death.

Specific compounds which may be useful to administer in combination with high pressure impulse transients include antibiotics, cytotoxic compounds, light activated dyes and salicylates. Suitable antibiotics include aminoglycosides such as kanamycin, neomycin, gentamycin, tobramycin, amikacin, netilmicin; streptomycin; and erythromcyin.

Suitable cytotoxic compounds include but are not limited to cisplatinum and adriamycin.

Suitable light activated dyes include but are not limited to hematoporphyrin derivatives, benzoporphyrin derivatives and aminolevulinic acid.

High-pressure impulse transients provided to the patient are defined as those impulse transients with a pressure component of greater than 100 bars which have a fast rise time of less than 100 nanoseconds, preferably less than 10 nanoseconds, and are compressional impulses, meaning that there is no negative tensile component to the wave. These high pressure impulse transients are administered as discrete pulses with the total number of impulse transients administered to the patient being less than 3000, more preferably less than 100, and most preferably less than 50.

High pressure impulse waves may be generated by dielectric breakdown, laser-induced ablation, laser-induced plasma on metallic surfaces, rapid heating of any absorbing material, the use of high velocity projectiles, or the use of any other technique known in the art for creating high pressure impulse transients. Most preferably, laser-induced ablation is used to generate the impulse.

DETAILED DESCRIPTION

The drawings are first described.

Drawings FIG. 1 is a graph of the percent hemolysis of red blood cells versus increasing osmotic strength of the diluent saline for different combinations of cells, media and laser impulse dosages.

Therapy

Figure 1:
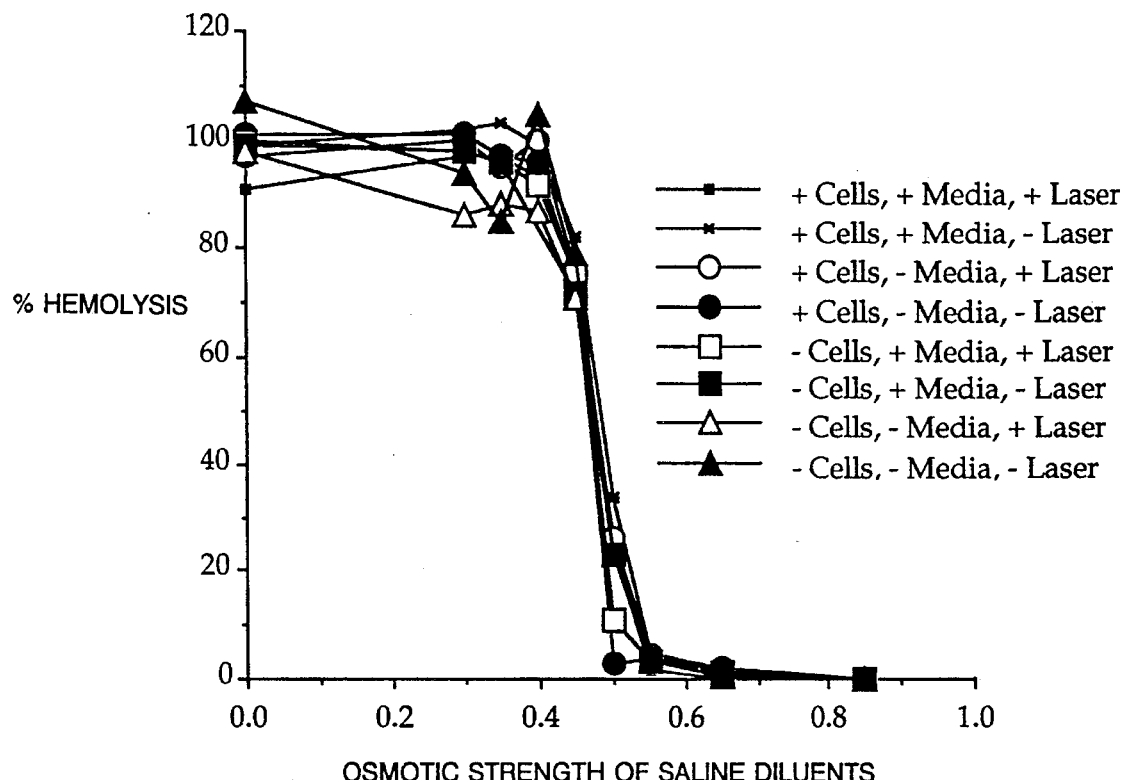

The invention provides non-localized administration of compounds of high therapeutic index such as aminoglycosides, aspirin, and cisplatinum, in combination with the localized administration of high-pressure impulses applied to the region of the proliferating diseased tissue. The therapeutic index (defined above) of a candidate compound can be routinely determined using the methods described below. The high-pressure impulse may be generated by any known means, including lasers, lithotriptors, or piezoelectric devices. The invention provides for the delivery of relatively few discrete pulses of high positive amplitude to the patient, rather than a larger number of low amplitude continuous waves which generally cause surrounding tissue damage. These high pressure impulses have the surprising effect of dramatically increasing drug delivery to the cells. As a result, lower levels of the therapeutic compound may be administered systemically to the patient.

Results described in the examples below indicate that the combination of drug delivery followed by a few carefully timed high pressure impulses provides a highly effective and localized method of cell killing in proliferating tissues. The method will advantageously provide a two-fold level of localization, which minimizes the generalized trauma to the patient. First, the chemotherapeutic compound of choice will naturally localize to the proliferative tissue due to the irregular vascularization of the proliferative growth. The drug will be rapidly cleared from the rest of the body during the pre-pressure wave time course. Secondly, high pressure impulses can be administered with highly localized effect to the area of the proliferative growth, sparing healthy tissues of the body. The healthy vital organs are spared from the combination of the compound administered at sub-toxic doses, and the use of an impulse which by itself has no unacceptable effect on tissue viability.

Because the drugs administered have little effect in the absence of a high pressure impulse, there should be little accompanying generalized toxicity in the patient outside the area of the tumor. The therapy can be administered either extracorporeally or during invasive surgery for tumor removal. Techniques for both methods of delivery are known to one skilled in the art.

Compounds Useful for High-pressure Impulse Transient Therapy

The high pressure impulse works in combination with the therapeutic compound by generally increasing passive cell permeability in the region of impulse administration. Thus, any compound with cytotoxic effect which may a) be effectively localized via the vasculature to proliferating cells and b) be administered in low toxicity dosages will potentially be useful in the invention. Specific compounds include cytotoxic compounds with acceptably low general toxicity at the dosage used and in the absence of impulse transients, antibiotics, light activated dyes, salicylates, and antibiotics such as aminoglycosides, e.g., kanamycin, neomycin, gentamycin, tobramycin, amikacin, netilmicin; streptomycin; and erythromcyin.

Suitable cytotoxic compounds include but are not limited to cisplatinum and adriamycin.

Suitable light activated dyes include but are not limited to hematoporphyrin derivatives, benzoporphyrin derivatives, aminoleuvinlic acid, and phthalocyanine.

Methods of Producing High Pressure Impulse transients

An impulse transient is defined as a high amplitude, fast rise time, compressional stress wave.

High amplitude fast rise time impulses can be generated by a variety of methods, including the following:

a) Dielectric breakdown induced by
   i) a high voltage spark (one example is the extracorporeal lithotriptor; Coleman et al., *Ultrasound Med. Biol.* 15:213–227 (1991); or
   ii) laser breakdown of, for example, water (Doukas et al., *Appl. Phys.* B53:237–245 (1991));

b) Laser generation of impulses mediated by such processes as ablation or plasma directly on the tissue or polymeric or metallic foils coupled to the tissue via gel or oil; (Zweig and Deutsch *Appl. Phys.* B54:76–82 (1992); Yang, *J. Appl. Phys.* 45:2601–2608 (1974); Wantanabe et al., *J. Invest. Dermatol.* 90:761–766, 1988));

c) Rapid heating of any absorbing material (Vodop'yanov et al., *Sov. Phys. JETP* 64:67–70 (1986)); or d) Use of a piezoelectric transducer (one example is the extracorporeal lithotriptors (Coleman et al. *Ultrasound Med. Biol.* 15:213–227, 1989)).

In addition to these techniques, there are a number of other methods that can be used to create high pressure impulses, such as explosion and high velocity projectiles.

The requirement of fast rise of the impulse can be achieved by a combination of generation of a fast deposition of energy on the target, e.g. by employing Q-switched (Fairand and Clauer *J. Appl. Phys.* 50:1497–1502 (1979)) or mode-locked lasers (Leung et al. *Phys. Rev.* B31:942–946 (1985)), while allowing the impulse to propagate a distance inside the material. This approach takes advantage of the non-linear properties of the target material. In this case, the rise of the high pressure impulse transients steepens to form a fast rise stress wave. The distance required to achieve this effect depends upon the characteristics of the material, the amplitude of the stress wave, and the initial rise time (Lamshev and Naugol'nykh *Sov. Phys. Acoustics* 27:357–371 (1981)).

The requirement that the impulse be compressional can be achieved by confinement of the target (Carome et al. *Appl. Phys. Lett.* 4:95–97 (1964)).

Pressure can be measured by:

1) transducers, such as quartz or PVDF (Polyvinyldenefluoride) (Dyer and Al-Dhahir, Proceeding Lasr-tissue Interactions, *SPIE* 1202:46–60 (1990)), 2) measuring the changes in the emission profile of dyes (e.g. anthracene (Huston et al. *Chem. Phys. Lett.* 118:267–270 (1985)) and semiconductors (e.g., Case, Leung et al. *Phys. Rev.* B31:942–946 (1985)), 3) measuring the speed of the impulse (Doukas et al., *Appl. Phys.* B53:237–245 (1991)), or 4) measuring the deflection of an optical beam Vogel and Lautervorn *J. Acoust Soc. Am.* 84:719–731 (1988).

General Method for Identifying Useful Compounds For High Pressure Impulse Transient Therapy:

Methods for determining compounds with cytotoxicity in a photodynamic therapeutic regimen may be determined using the techniques outlined in Example 1, below. In general, any cell type may be used to determine for the toxicity of a given compound prior to and in combination with the administration of high pressure impulse transients. The general protocol is as follows:

Cell culture. Immortalized cell lines are kept in tissue culture in the usual manner. Typically, EMT-6 mouse mammary carcinoma cells are utilized. The cells are then resuspended in R.P.M.I. 1640 (GIBCO) with 10% fetal bovine serum (FBS) (GIBCO). The cultures are incubated at 37° C. in at atmosphere of 5% $CO_2$. Cultures of $2\times10^6$ cells per ml were established in flat bottom culture plates (Fisher Scientific).

Gel. Denatured collagen (Knox gelatin) is added to phosphate buffered saline at 37° C. to make a 5% solution. Capillary tubes with 3 mil polyimide (Dupont, Wilmington, Del.) glued to one end are warmed to 37° C. 100,000 cells in 100 µl of the denatured collagen solution are added to each capillary tube at 37° C. The tubes are centrifuged at 1,200 RPM to bring the cells to the bottom. The tubes are placed in an ice bucket.

Impulse generation. The polyimide is irradiated with an argon-fluoride excimer laser at 400 mJ/cm$^2$ (14 ns, 193 nm). The repetition rate is 1 hertz.

Thymidine incorporation. Cell filled capillary tubes are put into the 37° C. water bath for 2 minutes. The polyimide is then removed from each capillary tube. The contents of each capillary tube are flushed with 0.5 ml complete medium into separate 5 ml test tubes containing 0.5 ml complete medium. These test tubes are spun at 3200 RPM for 10 minutes. After centrifugation the supernatant in each tube is aspirated and discarded. Cell pellets are then resuspended with 200 µl of complete medium with 0.25 µCi of $^3$[H]-thymidine (sp. ac. 6.7 CI/mM; New England Nuclear, Boston, Mass.) and plated in a 96 well, flat-bottom microtiter plate. The plate is incubated for 4 hours. The cells are then disrupted, and the contents are collected on glass fiber filter strips and washed freely using an automated harvester (MASH II, Microbiological Associates, Walkersville, Md.). The dried filter papers are suspended in scintillation fluid and the radioactivity measured in a Beckman LS 3801 liquid scintillation spectrometer. The mean of the radioactive counts per minute (cpm) of the sample for each condition is calculated, and the means for cultures subjected to high pressure impulses are expressed as a percentage of the control cultures.

Determination of cell toxicity. Candidate compounds are tested for their cytotoxicity by plating 100,000 cells/well in a 96-well plate and adding different quantities of the compound to different wells. All concentrations are replicated in 5 wells for accuracy. The quantities to be tested are generally known to one skilled in the art; however, a typical experiment would test the following concentrations (in µg/ml): 0.0, 0.001, 0.01, 0.1, 1.0, 2.0, 4.0, and 10.0. The cells are then incubated overnight and then the thymidine incorporation assay as described above is utilized. The toxic dose is considered to be that dose where the means counts decreased by 20% relative the interested control. The next lower concentration is then used for the subsequent experiments.

The general protocol for determining synergistic effects with test compound and high pressure impulse transients involves the following steps:

1. Determine the toxicity of experimental drug of interest as described above.
2. Incubate cells with experimental drug overnight at the highest non-toxic concentration that was tested.
3. Wash the cells three times with RPMI and then put the cells on ice until needed.
4. Make the gel solution with and without the experimental drug.
6. Make the capillary tubes with the cells in the gel as described above. Typically 40 tubes will be necessary to perform all the groups listed in the table below in 5 replicates.
7. Expose cell in gels to impulses.
8. Assay cells for thymidine incorporation.

Table of Groups to Test

| Group | Incubate Cells with Experimental Drug | Experimental Drug in Gel | Pressure Transients |
|---|---|---|---|
| 1 | + | + | + |
| 2 | + | + | − |
| 3 | + | − | + |
| 4 | + | − | − |
| 5 | − | + | + |
| 6 | − | + | − |
| 7 | − | − | + |
| 8 | − | − | − |

Manner of Identifying the Effective High Pressure Impulse Transient

The effective high pressure impulse is that which decreases cell viability by 25 percent or more when administered in combination with an otherwise low toxicity dose of the therapeutic compound.

In Vivo Testing of Useful Compounds for High Pressure Impulse Chemotherapy
Animal Models A variety of animal models have been developed to predict the potential effectiveness of therapeutic modalities for the treatment of human diseases. Classical model systems of neoplasms use three basic strategies.

Transplantable tumors where the tumor cells are introduced into a naive animal and are passed from animal to animal (Block et al., *Oncology* 34:110–113, 1977). These systems are easy to setup, cost efficient to do large numbers of animals, and the tumors from different animals show similar characteristics. The tumors show differences in the tumor development and vasculature as compared to spontaneous tumors.

Tumors can be induced in animals by such agents as chemical carcinogens and ionizing and non-ionizing radiation. These models have variable incidence of production, develop vasculature and mesenchymal alterations similar to primary tumors and share many biological properties of primary tumors. The disadvantages of these systems include the length of time to develop the tumors, the expense of the experiment, and dissimilarity of the tumors.

Spontaneous tumors in animals share the greatest similarity of biological properties of human tumors; however, the expense and time to develop the tumors can be great and the tumors show the most dissimilarities between animals. Recently developed transgenic mice which develop tumors may alter this last category by decreasing the expense and producing more similar tumors while maintaining the properties of spontaneous tumors (Pattengale et al., *Am. J. Pathol.* 135:39–61, 1989).

In addition to animal models of neoplastic diseases, there are a wide variety of models of non-neoplastic diseases. Generally these model systems introduce an agent that produces an injury that is similar to the disease being studied. Arthritis is a disease for which a number of model systems have been developed. The models can be divided into four categories, hypersensitization arthritis, chemical arthritis, rheumatoid factors, and spontaneous arthritis in animals (Sokoloff, *Int. Rev. Exp. Pathol.* 26:107–145, 1984; Magilavy, *Clinical Orthopedics* 259:38–45, 1990). In hypersensitization arthritis, antigen is introduced into animals that are have been sensitized to that antigen. The resulting immune response produces injury and an inflammatory response. In chemical arthritis, the immediate damage is produced by the injected reagent such as zymosan or collagenase or the chemical may induce the damage as in the lysosomal membrane destabilizers. Systemic administration of rheumatoid factors (antibodies to antibodies) may produce arthritis in addition to other vascular phenomena. Finally, there are a variety of spontaneous models of arthritis such as the MRL/1 mice which develop a lupus-like illness which includes an arthritis.

Other carcinoma disease animal models are described in the following: Bachor et al., *J. Urol.* 147:1404–10, 1992; Richter et al., *British J. Cancer* 63:87–93, 1991; Yumita et al., *Jpn. J. Cancer Res.* 81:304–308, 1990; Berens et al., *J. Urol.* 142:1090–1094, 1989; and Holmes et al., *J. Urol.* 144:159–163, 1990.

These models may be used to confirm the therapeutic promise of compounds with demonstrated effectiveness in the assays ascribed above and below. For example, modifications of the protocols outlined above may be performed using the antigen induced rat or rabbit arthritis models, or any one of the many carcinoma animal models which exist in the art.

Determination of the compound dosage and time course to achieve a 2:1 or greater concentration ratio in the effected tissues relative to the surrounding tissues is routine to one skilled in the art of pharmaceutical administration. Two approaches are commonly used to assay directly the quantity of drug in the tumor (or other diseased tissue) and the surrounding tissues. First, samples are obtained of tumor and tissues from animals/patients who have received different dosage and timing protocols. The quantity of drug in each tissue is then measured either chemically, or if there is a unique optical signal such as fluorescence, then by quantitative microscopy or laser-induced fluorescence. Impulses effective to yield the desirable result may be obtained using any one of the impulse generating devices indicated above and calibrated so as to yield an impulse within the parameters described above. One skilled in the art may readily determine the optimal impulse parameters from within the provided scale for a given cell type, body region, and compound by means well known in the art.

It is understood that various other modifications of the method of the invention will be apparent and can readily be made by those skilled in the art without departing from the scope and spirit of the invention. In particular, it will be straightforward to evaluate compounds other than those specifically listed for their usefulness in the general treatment protocol described. In addition, it will also be straightforward to identify diseased cell types other than those specifically listed which will be effectively treated using the methods of the invention.

The following examples are included to illustrate but not limit the invention.

EXAMPLE 1

Tumor Cell Killing By Drugs

Overview of protocols

The experimental design is outlined in the general protocol. In brief, cell lines are used to insure a uniform group of test cells for all aspects of the experiment. There are three sets of variables used to determine effective cell killing by a given compound: 1) preincubation of the cells with the test compound, 2) presence of the compound in the surrounding media or gel, and 3) the presence or absence of the use of impulse transients. There are eight possible combinations of these variables, all of which should be tested.

Sample Experiment

EMT-6 cells were used to test the effects of the compound Photofrin II. Five repetitions were done for each combination tested, giving a total of 40 tubes tested. Approximately 100,000 cells were present in each tube. An ArF excimer laser was used and the energy parameters were as follows: 400 mJ/sonimeter$^2$ was used to strike a polyimide target which delivers approximately 400 bar impulse transients and blocks light, heat transfer. A total 10 pulses were administered to each tube.

Cells were incubated with and without 1 μg/ml of Photofrin II overnight, followed by the dilution of cells to yield cell suspension of tumor cells, as described above. Cells were then placed in a liquid gel with and without 1 μg/ml of photofrin II. This was followed by exposure of cells to impulses. Following administration of impulses as indicated above, cells are incubated with tritiated thymidine. Thymidine incorporation is measured by recording counts using a scintillation counter. The results are summarized below.

Results summarized by group

| # | Incubate Cells with Photofrin | Photofrin II in Gel | Pressure Transients | Mean Counts | SD |
|---|---|---|---|---|---|
| 1 | + | + | + | 40,923 | 22,055 |
| 2 | + | + | − | 103,748 | 21,297 |
| 3 | + | − | + | 130,326 | 23,569 |
| 4 | + | − | − | 115,560 | 24,864 |
| 5 | − | + | + | 72,620 | 24,189 |
| 6 | − | + | − | 72,070 | 20,182 |
| 7 | − | − | + | 79,976 | 33,320 |
| 8 | − | − | − | 60,281 | 13,518 |

Results Presented as Rations of Lased and Not Lased Data

| Incubate Cells with Photofrin II | Photofrin II in Gel | Ratio of Shock to No Shock Data in % |
|---|---|---|
| − | − | 132.7% |
| − | + | 100.8% |
| + | − | 112.8% |
| + | + | 39.4% |

Results of Drug Testing

Percent indicates the decrease in cell viability of cells exposed to an impulse relative cells not exposed to an impulse.

Drugs with impulse-enhanced cytotoxicity:

| | |
|---|---|
| Photofrin II | 24.3% |
| Prodan | 60.7% |
| Rhodamine 123 | 72.5% |
| Tetrabrominated rhodamine | 19.7% |
| Tetracycline | 27.8% |
| Cisplatinum | 34.0% |

Drugs with no impulse-enhanced drug cytotoxicity
Chloro-aluminum sulfonated phthalocyanine 93.7%

Summary of Compound Testing

These screening assays show that the high pressure impulses can enhance the compound cytotoxicity of a variety of compounds when these compounds are administered at levels that are not normally toxic to the cells. A variety compounds show impulse enhanced cytotoxicity, as indicated in the table. However, chloro-aluminum sulfonated phthalocyanin failed to demonstrate this effect.

The most effective regimen occurs when the compound is both inside the cell and in the surrounding media at the time of exposure to the impulses. These conditions are present in many tumors and inflammatory conditions where there is an increased quantity of drug in the cells and extracellular matrix due to the increased and leaky vascularization of proliferating tissues.

EXAMPLE 2

Osmotic Fragility of Cells

Overview of protocols

To address whether the impulse enhanced drug cytotoxicity is due to alterations in osmotic fragility of the cell membrane or other physical factors the following experiments were performed. Human red blood cells were treated as a standard cell membrane preparation. The same eight groups detailed in the general protocol, above, were utilized. The assay utilized the standard laboratory testing kits from Becton-Dickinson (Unopette Test 5830, Rutherford, N.J.) for RBC osmotic fragility.

Sample Experiment

Human red blood cells were used to test the effects of the compound cisplatinum. Five repetitions were done for each combination tested, giving a total of 40 tubes tested. An ArF excimer laser was used and the energy parameters were as follows: 400 mJ/sonimeter$^2$ was used to strike a polyimide target which delivers approximately 400 bar impulse transients and blocks light, heat transfer. A total 10 pulses were administered to each tube.

Summary of Fragility Testing

The data for one experiment is presented in graphic form in FIG. 1. These experiments have shown that there is no alteration in the cell membrane fragility which correlates with the alterations in cell cytotoxicity.

EXAMPLE 3

Effect of Increasing Numbers of Impulses

Overview of protocol:

The experimental design is outlined in the aforementioned general protocol. In brief, cell lines are used to provide a uniform group of cells to test. There are three sets of variables: preincubation of the cells with the drug, drug in the surrounding media or gel, and the use of impulse transients. There are eight possible combinations of these variables, all of which should be tested. This protocol is used to screen for the impulse parameters which proved enhanced cell killing.

Sample High Pressure Impulses with Photofrin II.

EMT-6 cells were used to test the effects of the compound Photofrin II. Five repetitions were done for each combination tested, giving a total of 40 tubes tested. Approximately 100,000 cells were present in each tube. An ArF excimer laser was used and the energy parameters were as follows: 16% of full energy was used to strike a polyimide target which delivers approximately 400 bar impulse transients and blocks light and heat transfer. A total 10 pulses were administered to each tube. Specific Protocol:

Cells were incubated with 1 µg/ml of photofrin II overnight. Single cell suspensions of tumor cells were then made in PBS. Gels with Photofrin II were then constructed and the treated cells were placed into these liquid gels. Gel were the allowed to solidify. Cells were then exposed to high pressure impulses in the gel matrix. Following high pressure impulse administration cells were measured with tritiated thymidine. Counts in scintillation counter to determine the extent of cell proliferation. Results of Experiment

| Group | Photofrin Overnight | Photofrin Gel | # Pulses | Mean Counts | S.D. |
|---|---|---|---|---|---|
| 1 | + | + | 0 | 223,531 | 13,744 |
| 2 | + | + | 1 | 166,809 | 10,485 |
| 3 | + | + | 5 | 119,358 | 2,192 |
| 4 | + | + | 10 | 68,762 | 11,527 |
| 5 | + | + | 50 | 66,762 | 4,664 |
| 6 | + | + | 100 | 44,268 | 8,605 |

S.D. = standard deviation

Figure 2:
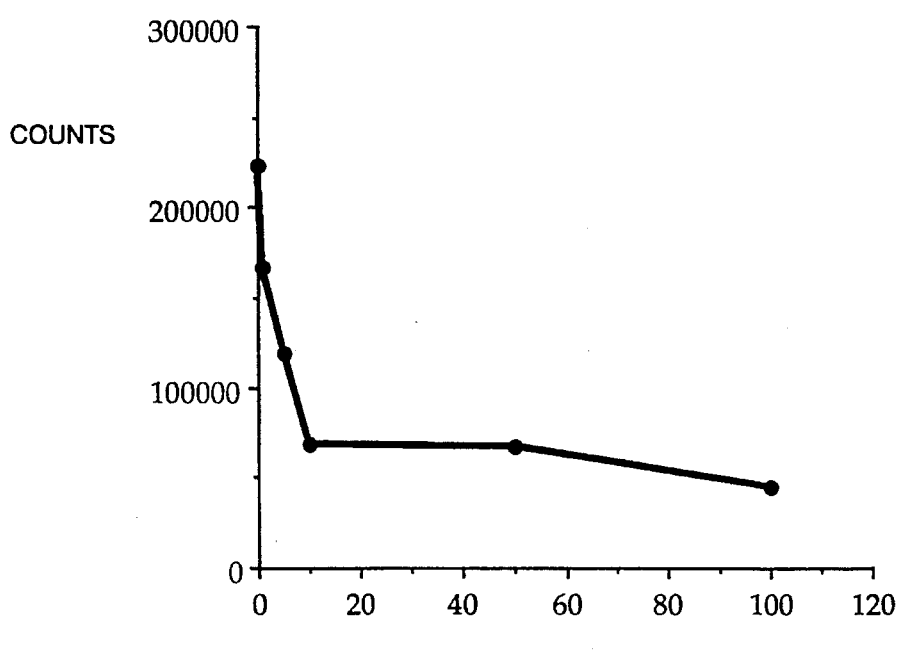
FIG. 2 is a graph of thymidine uptake in cells following a variable number of high pressure impulses.

This data is summarized in FIG. 2.

These experiments show that at sublethal doses of a given compound, the number of impulses is additive with two different domains. Initially, each pulse produces marked decreases in cell survival; however, after a small number of pulses, the additive effect is markedly decreased.

EXAMPLE 4

Experiments Showing Impulse Enhanced Drug Uptake

Overview of protocols

The hypothesis for these experiments is that the impulses enhance the intracellular drug delivery from the surrounding media. These experiments measure the amount of drug that is in the cells using a fluorimeter.

Sample Experiment to determine Impulse enhanced drug uptake.

EMT-6 cells were used to test the effects of the compound Photofrin II. Five repetitions were done for each combination tested, giving a total of 40 tubes tested. The concentration of Photofrin II used was 1 µg/ml Approximately 100,000 cells were present in each well. An ArF excimer laser was used and the energy parameters were as follows: 16% of full energy was used to strike a polyimide target which delivers approximately 400 bar impulse transients and blocks light and heat transfer. A total 10 pulses were administered to each tube.

Cells were incubated with and without 1 µg/ml of Photofrin II overnight. Subsequent single cell suspension of tumor cells were made and cells were placed in liquid gel with and without 1 µg/ml of Photofrin II. Cells were then exposed to high pressure impulses followed by lysis in 0.1M NaOH. Fluorescence was then measured using a fluorimeter.

Figure 3:
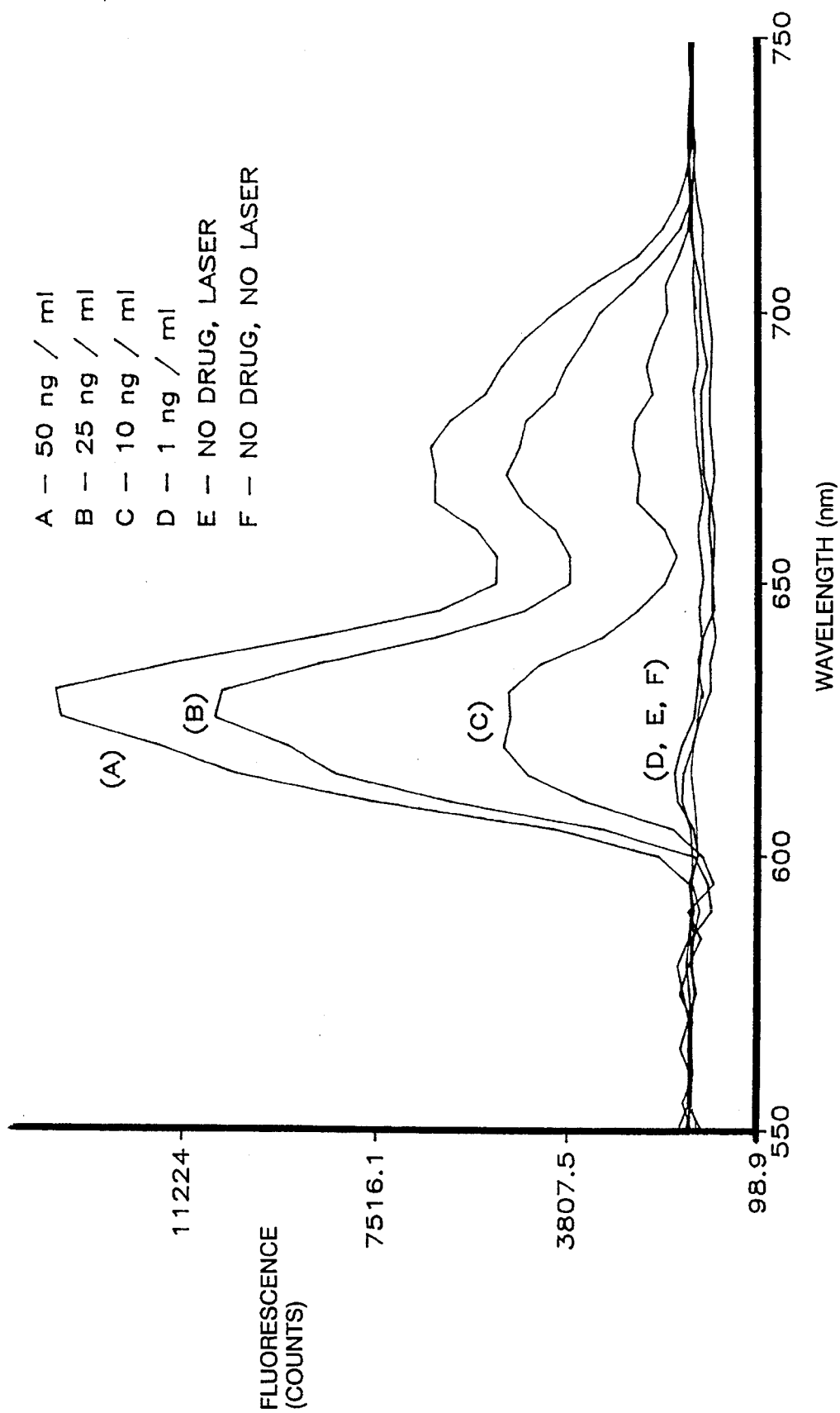
FIG. 3 is a graph of photofrin uptake by EMT6 cells for increasing drug concentrations.
Figure 4:
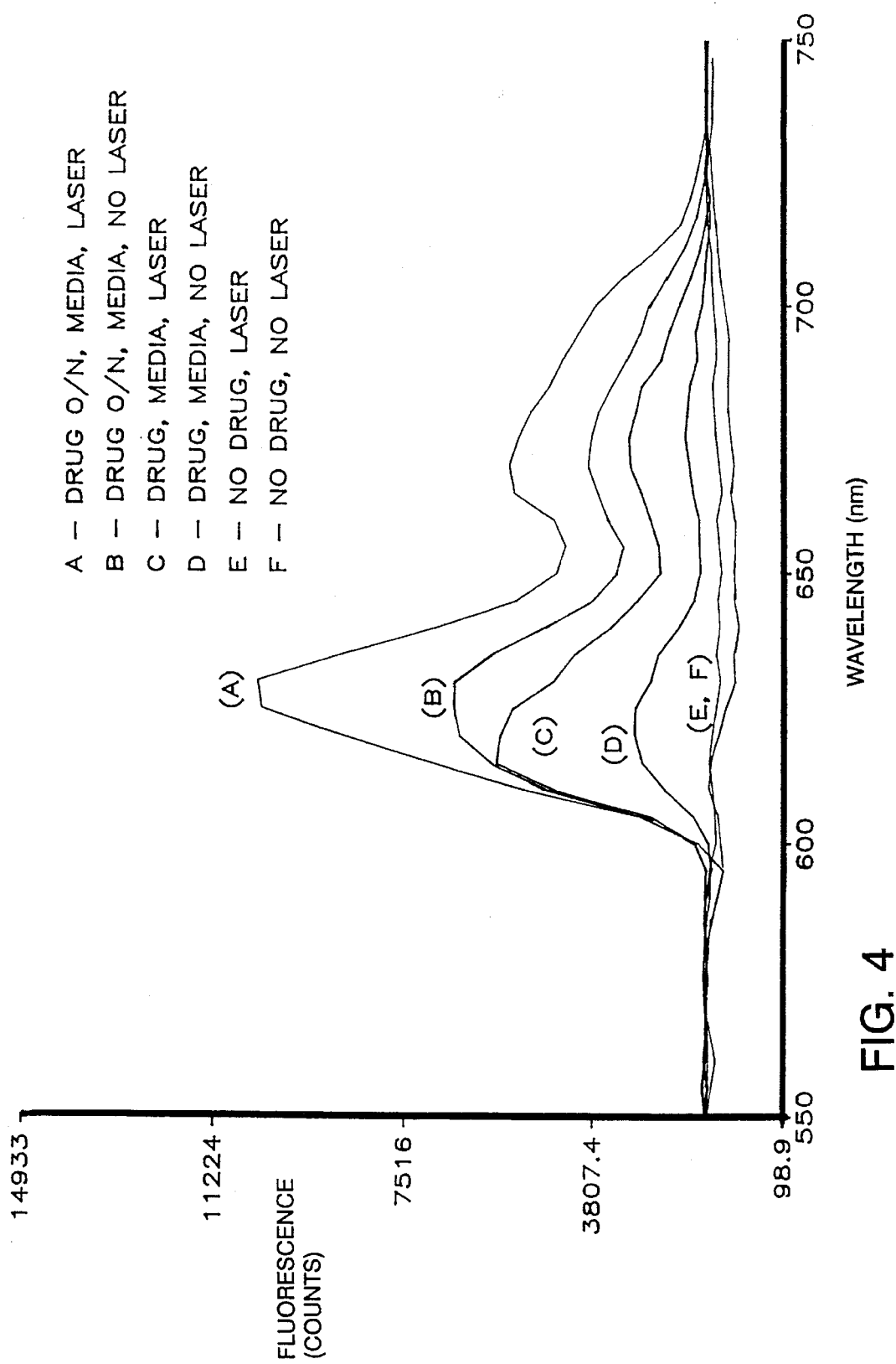
FIG. 4 is a graph of photofrin in uptake by EMT6 cells following various incubation regimes and high pressure impulse dosages.

Results:

The results are shown in graph form in FIGS. 3 and 4. The FIG. 3 shows the calibration curves. These curves are generated by lysing the same number of cells as is used in the experiment and adding a known quantity of drug. FIG. 4 shows the results from this experiment. For each condition, there was at least a two fold increase in intracellular concentration of the drug following exposure to the impulses.

Other embodiments are within the following claims.

All references cited above are hereby incorporated by reference.

What is claimed is:

1. A method of treating a patient with a disease characterized by the presence of a tumor, said method comprising:

administering to said patient a compound having a therapeutic index of at least 50, and exposing a region of diseased tissue to at least one high-pressure compressional impulse transient when a level of said compound in surrounding healthy tissues is less than 50 percent of a level of said compound present in said region of diseased tissue, said exposing increasing permeability in cells comprised in said exposed region to facilitate localized delivery of said compound to said region of diseased tissue.

2. Method of claim 1, wherein said compound is a light activated dye compound.

3. Method of claim 1, wherein said disease is a solid neoplasm.

4. Method of claim 1, wherein administration of said impulse transients is during invasive surgery.

5. The method of claim 1, wherein said high pressure compressional impulse transient is generated by laser-induced plasma on a metallic surface.

6. The method of claim 1, wherein said high pressure compressional impulse transient is generated by laser-induced ablation.

7. The method of claim 1, wherein said high pressure compressional impulse transient is generated by rapid heating of an absorbing material.

8. The method of claim 7, wherein said rapid heating of said absorbing material is generated by a laser.

9. The method of claim 1, wherein said high pressure compressional impulse transient is generated by laser-induced plasma on a metallic surface.

10. The method of claim 1, wherein said high pressure compressional impulse transient is generated by laser-induced ablation.

11. The method of claim 1, wherein said high pressure compressional impulse transient is generated by rapid heating of an absorbing material.

12. The method of claim 11, wherein said rapid heating of said absorbing material is generated by a laser.

13. A method of treating a patient with a disease characterized by the presence of a tumor, said method comprising:

administering to said patient a compound selected from the group consisting of Photofrin II, Prodan, Rhodamine 123, tetrabrominated rhodamine, tetracycline and cisplatinum, and exposing a region of diseased tissue to at least one high-pressure compressional impulse transient when a level of said compound in surrounding healthy tissue is less than 50 percent of a level of said compound present in said region of diseased tissue, said exposing increasing permeability in cells comprised in said exposed region to facilitate localized delivery of said compound to said region of diseased tissue.

* * * * *